United States Patent
Dandiker et al.

(10) Patent No.: US 12,208,169 B2
(45) Date of Patent: *Jan. 28, 2025

(54) TESTOSTERONE TRANSDERMAL SPRAY WITH FILM

(71) Applicant: CELISTA PHARMACEUTICALS LLC, Edina, MN (US)

(72) Inventors: Yogesh Dandiker, Edina, MN (US); Maulik K. Panchal, Maple Grove, MN (US)

(73) Assignee: CELISTA PHARMACEUTICALS LLC, Edina, MN (US)

( * ) Notice: Subject to any disclaimer, the term of this patent is extended or adjusted under 35 U.S.C. 154(b) by 147 days.

This patent is subject to a terminal disclaimer.

(21) Appl. No.: 18/054,816

(22) Filed: Nov. 11, 2022

(65) Prior Publication Data

US 2023/0143438 A1    May 11, 2023

Related U.S. Application Data (63) Continuation of application No. 16/960,428, filed as application No. PCT/US2019/013047 on Jan. 10, 2019, now Pat. No. 11,523,994.

(60) Provisional application No. 62/615,865, filed on Jan. 10, 2018.

(51) Int. Cl.
| | |
|---|---|
| A61K 9/70 | (2006.01) |
| A61K 31/568 | (2006.01) |
| A61K 47/10 | (2017.01) |
| A61K 47/14 | (2017.01) |
| A61K 47/32 | (2006.01) |
| A61M 35/00 | (2006.01) |
| A61M 39/22 | (2006.01) |

(52) U.S. Cl.
CPC .......... *A61K 9/7015* (2013.01); *A61K 31/568* (2013.01); *A61K 47/10* (2013.01); *A61K 47/14* (2013.01); *A61K 47/32* (2013.01); *A61M 35/003* (2013.01); *A61M 39/22* (2013.01)

(58) Field of Classification Search
None
See application file for complete search history.

(56) References Cited

U.S. PATENT DOCUMENTS

| | | | |
|---|---|---|---|
| 4,520,179 A | 5/1985 | Barabas et al. | |
| 6,010,716 A | 1/2000 | Saunal et al. | |
| 6,299,900 B1 | 10/2001 | Reed et al. | |
| 6,503,894 B1 | 1/2003 | Dudley et al. | |
| 6,750,291 B2 | 6/2004 | Kim et al. | |
| 6,818,226 B2 | 11/2004 | Reed et al. | |
| 6,923,983 B2 | 8/2005 | Morgan et al. | |
| 6,958,154 B2 | 10/2005 | Brandt et al. | |
| 6,962,691 B1 | 11/2005 | Lulla et al. | |
| 7,030,104 B2 | 4/2006 | Gray et al. | |
| 7,186,706 B2 | 3/2007 | Rosario-Jansen et al. | |
| 7,214,381 B2 | 5/2007 | Carrara et al. | |
| 8,067,399 B2 | 11/2011 | Lehman et al. | |
| 8,268,346 B2 | 9/2012 | Simes et al. | |
| 8,895,053 B2 | 11/2014 | Grenier et al. | |
| 8,980,309 B2 | 3/2015 | Carrara et al. | |
| 9,078,810 B2 | 7/2015 | Setiawan et al. | |
| 9,180,194 B2 | 11/2015 | Dipietro et al. | |
| 9,289,586 B2 | 3/2016 | Bayly et al. | |
| 2002/0028235 A1 | 3/2002 | Reed et al. | |
| 2005/0002868 A1 | 1/2005 | Gonda et al. | |
| 2007/0196452 A1 | 8/2007 | Zhang et al. | |
| 2007/0219171 A1 | 9/2007 | Lulla et al. | |
| 2008/0261896 A1 | 10/2008 | Tanaka et al. | |
| 2009/0075963 A1 | 3/2009 | Levinson et al. | |
| 2009/0099149 A1 | 4/2009 | Liu et al. | |
| 2010/0279988 A1 | 11/2010 | Setiawan et al. | |
| 2013/0085166 A1 | 4/2013 | Makra | |
| 2015/0094290 A1 | 4/2015 | Morgan et al. | |
| 2016/0022820 A1 | 1/2016 | Setiawan et al. | |
| 2017/0128462 A1 | 5/2017 | Simes et al. | |
| 2017/0157377 A1 | 6/2017 | Chang et al. | |
| 2017/0157378 A1 | 6/2017 | Chang et al. | |

FOREIGN PATENT DOCUMENTS

| | | |
|---|---|---|
| WO | 2000/045795 A2 | 8/2000 |
| WO | 2005/041943 A1 | 5/2005 |
| WO | 2018/087779 A1 | 5/2018 |
| WO | 2020/010205 A1 | 1/2020 |

OTHER PUBLICATIONS

Cappelletti et al., "Increasing Women's Sexual Desire: The Comparative Effectiveness of Estrogens and Androgens," Horm. Behav 78:178-193 (2016).
Davis et al., "Testosterone for Low Libido in Postmenopausal Women Not Taking Estrogen," NEJM 359(19):2005-2017 (2008).
Davis et al., "Safety and efficacy of a testosterone metered-dose transdermal spray for treating decreased sexual satisfaction in premenopausal women," Ann. Intern. Med. 148:569-577 (2008).
Kathe et al., "Film Forming Systems for Topical and Transdermal Drug Delivery," Asian Journal of Pharmaceutical Sciences 12:487-497 (2017).
Kotiyan et al., "Eudragits: role as crystallization inhibitors in drug-in-adhesive transdermal systems of estradiol," Eur. J. Pharmaceutics Biopharmaceutics 52:173-180 (2001).
Leichtnam et al., "Formulation and evaluation of a testosterone transdermal spray," J. Pharmaceutical Sci. 95(8):1693-1702 (2008).
Lu et al., "Preparation and Characterization of a Metered Dose Transdermal Spray for Testosterone," Acta Pharmaceutica Sinica 3(6):392-399 (2013).

(Continued)

*Primary Examiner* — Nannette Holloman
(74) *Attorney, Agent, or Firm* — MEDLER FERRO WOODHOUSE & MILLS PLLC (57) ABSTRACT

The invention relates to a sprayable liquid solution for the transdermal delivery of testosterone comprising testosterone, a penetration enhancer, and a film forming excipient, and to methods of treatment using this composition.

16 Claims, 6 Drawing Sheets

(56) References Cited

OTHER PUBLICATIONS

Malik et al., "Episodic transdermal delivery of testosterone," Mol. Pharmaceutics 9:1537-1543 (2012).

Misra et al., "Biphasic testosterone delivery profile observed with two different transdermal formulations," Pharmaceut. Res. 14(9):1264-1268 (1997).

Nicolazzo et al., "Synergistic enhancement of testosterone transdermal delivery," J. Controlled Release 103:577-585 (2005).

Schroeder, et al., "Delivery of ethinylestradiol from film forming polymeric solutions across human epidermis in vitro and in vivo in pigs," J. Controlled Release 118:196-203 (2007).

The International Search Report and the Written Opinion of the International Searching Authority mailed Apr. 8, 2019 in international application No. PCT/US2019/013047.

TESTOSTERONE TRANSDERMAL SPRAY WITH FILM

BACKGROUND

Testosterone is a primary male sex hormone that plays a key role in the development of male reproductive tissues, and secondary sexual characteristics such as increased muscle and bone mass. Testosterone levels gradually decrease as men age. In addition, some younger men suffer from primary hypogonadism, or hypogonadotropic hypogonadism, conditions in which insufficient testosterone is produced by the body. Testosterone deficiency is usually associated with adverse effects on body composition, bone density, sexual function, and mood, and may also increase cardiovascular risk. Testosterone replacement therapy may be prescribed to counteract testosterone deficiency.

Currently, testosterone replacement therapy products include a transdermal gel (Androgel®, Testim®, Fortesta®), transdermal solution (Axiron®), transdermal patch (Androderm®), injection (Delatestryl®, Aveed®) and buccal tablet (Striant®). Most of these are transdermal dosage forms, one is an injection, and one is an oral transmucosal dosage form. In addition, orally ingested tablet and capsule forms of methyltestosterone are available.

The oral ingestion route requires administration of a high testosterone dose due to hepatic first-pass metabolism in the liver, while intramuscular administration is painful and can result in supra-physiological testosterone serum concentrations. Testosterone characteristics such as a relatively low molecular weight and moderate lipophilicity make the transdermal route the most suitable route for the administration of testosterone.

Existing, transdermal gel and transdermal solution formulations are inconvenient dosage forms as they must be applied over large surface areas to achieve target plasma levels.

A more significant disadvantage of these formulations is that topical application of testosterone, without a protective cover or barrier over the area, may leave unabsorbed drug exposed creating a risk of transfer of testosterone to other persons. Transfer of testosterone may cause serious side-effects in female partners and especially prepubertal children.

In fact, topical testosterone creams, gels and solutions are associated with a significant risk for secondary testosterone exposure (Lewis and Goldstein, 2009). Numerous case reports have demonstrated the occurrence of precocious puberty or virilization in infants and young children following contact with male parents treated with topical testosterone products (Brachet et al., 2005; Bhowmick et al., 2007; Cavender et al., 2011; Franklin, 2011; Kunz et al., 2004; Martinez-Pajares et al., 2012; Nelson et al., 2013; Stephen et al., 2008; Yu et al., 1999). Virilization of adult women has also occurred following secondary testosterone exposure from their male partners (de Ronde, 2009; Kathiresan et al., 2011; Merhi and Santoro, 2007).

Specific changes following secondary testosterone exposure in children include gynecomastia, rapid growth, pubic hair, enlarged penis and clitoris and facial acne (Brachet et al., 2005; Bhowmick et al., 2007; Cavender et al., 2011; Franklin, 2011; Kunz et al., 2004; Lewis and Goldstein, 2009; Nelson et al., 2013; Yu, 1999). Adult women have reported hirsutism, clitoral enlargement, scalp alopecia, irregular menses, deepening voice and increased muscle mass (Brachet et al., 2005; de Ronde, 2009; Kathiresan et al., 2011; Merhi and Santoro, 2007). Symptoms generally resolve after exposure to testosterone has ended, although in one case, enlarged penis persisted in a young boy (Yu, 1999).

As a result of the risk of secondary testosterone exposure, AndroGel® (topical gel) and Axiron® (topical solution) are required to display the following black box warning in the approved product label:

WARNING: SECONDARY EXPOSURE TO TESTOSTERONE

Virilization has been reported in children who were secondarily exposed to [testosterone gel/topical testosterone products].

Children should avoid contact with unwashed or unclothed application sites in men using [testosterone gel/AXIRON®].

Healthcare providers should advise patients to strictly adhere to recommended instructions for use.

(See First page of Prescribing Information for AndroGel® (rev. October 2016) and Axiron® (rev. July 2017)).

While the case reports described above involve skin-to-skin contact, secondary testosterone exposure from contaminated clothing or bed linens may also be possible (Mazer et al., 2005). A recent study demonstrated the amount of residual testosterone present on the clothing of volunteer subjects using a topical testosterone solution (Axiron® [testosterone]topical solution, for topical use. Lilly USA, LLC Indianapolis, IN; Satonin et al., 2016). Healthy adult men (N=12) applied 1.5 mL of testosterone 2% solution to both axillae (total testosterone dose: 120 mg). After waiting ≥3 minutes, subjects dressed in long-sleeved cotton T-shirts. After being worn for 12 hours, the T-shirts were removed and a 10 cm$^2$ sample of t-shirt was cut out from each armpit area for testosterone quantification before and after laundering with samples of unworn textiles. Mean testosterone in unwashed worn T-shirts was 7,603 µg representing 13% of the dose to one armpit with high between-subject variability (3,359 µg to 13,069 µg). Mean testosterone in worn, laundered T-shirts was 260 µg representing 3% of the dose to one armpit (range, 7.55 µg to 1,343 µg). Mean transferred testosterone to other textiles during laundering ranged from 69 µg on texturized Dacron 56T Double to 10,402 µg on 87/13 nylon/Lycra knit, representing 0.0382% to 5.78% of the dose to one armpit.

Another disadvantage of Axiron® topical solution is that the volume of solution applied is relatively large, and the solution can drip or run, so some of the solution may be spilled during application, resulting in an inaccurate dose. Axiron® topical solution is provided in a pump bottle and is intended for application to the axilla (the armpit area) using an applicator. Depressing the pump once dispenses 30 mg of testosterone. The following directions for use are provided to the patient in the Axiron® prescribing information:

To dispense the solution, position the nozzle over the applicator cup and carefully depress the pump fully once. Ensure that the liquid is directed into the cup. The cup should be filled with no more than 30 mg (1 pump actuation) of testosterone. Dosing that requires greater than one pump actuation must be applied in increments of 30 mg.

Keeping the applicator upright, patients should place it up into the axilla and wipe steadily down and up into the axilla. If the solution drips or runs, it can be wiped back up with the applicator cup. The solution should not be rubbed into the skin with fingers or hand. The process is then repeated with application of 30 mg of testosterone (1 pump actuation) to the other axilla to achieve a total of 60 mg of testosterone applied. When repeat application to the same axilla is required, the axilla should be allowed to dry completely before more AXIRON is applied.

After use, the applicator should be rinsed under room temperature, running water and then patted dry with a tissue. The applicator and cap are then replaced on the bottle for storage.

(See, Axiron® Prescribing Information, page 4 (rev. July 2017). These instructions are fairly lengthy and complicated.

Transdermal patches may avoid transference, but have other drawbacks that significantly reduce patient acceptance and compliance. One of these disadvantages is that the patch can cause skin irritation due to occlusion. Another disadvantage is that good adhesion of the patch requires shaving of the scrotal skin.

For the various reasons described above, there is a need for an improved transdermal formulation of testosterone.

SUMMARY

The invention provides an improved transdermal testosterone formulation. The invention relates to a sprayable liquid solution for the transdermal delivery of testosterone, and to a method of providing testosterone replacement therapy by administering this composition. The composition contains a film forming excipient, which leaves a film on the skin. This film is washable, meaning that it can be removed with water or soap and water. This film is a barrier that prevents transference of the testosterone to others, such as the user's partner or child. In addition, the formulation provides an effective dose of testosterone in a small volume spray that is easy to apply.

BRIEF DESCRIPTION OF THE DRAWINGS

The foregoing and other features and aspects of the present invention can be better understood from the following description of embodiments and as illustrated in the accompanying drawings. The accompanying drawings, which are incorporated herein and form a part of the specification, further serve to illustrate the principles of the present invention.

DETAILED DESCRIPTION

The present invention is directed to a sprayable liquid solution for the transdermal delivery of testosterone, and to a method of providing testosterone replacement therapy using this composition. The composition contains a film forming excipient that leaves a film on the skin after the spray has dried. This film is a barrier that prevents transference of the testosterone from the applied area to others, such as the user's partner or child. This quality provides a large advantage over testosterone topical products such as Axiron® and Androgel®. Another significant advantage over these products, and over patches is that the film is washable, meaning that it can be removed with water or soap and water. The film will be washed off, e.g., when showering. In other embodiments, the film may be removed with alcohol wipes.

Yet another advantage over testosterone topical products such as Axiron®, Androgel®, or testosterone patches, is that the film left on the skin is breathable. This characteristic may be measured using the technique described in Example 9 below.

The volume of spray administered in a single dose is preferably about 250 μL, or about 200 μL, (microliters) of solution per actuation containing about 30 mg of testosterone. In another preferred embodiment, a single dose is two actuations (sprays) each actuation delivering about 100 μL of solution containing about 15 mg of testosterone. Thus, in this embodiment, the spray is administered twice to apply a single dose, with the second actuation performed within a few minutes of the first. The desired dose of testosterone may also be divided into even smaller doses with more than two actuations needed to deliver a total dose of, e.g., 30 mg of testosterone.

These volumes are one sixth, or less, of the volume of a single dose of Axiron® solution (30 mg/1.5 mL/per actuation), but deliver the same amount of testosterone. Thus, the spray of the invention is much easier to apply than Axiron® because of the reduction in volume. The lower volume, and use of a spray pump greatly simplify application of the formulation. Although this spray is intended for application under the arm or to the upper arm, inclusion of a film forming excipient to reduce the risk of secondary testosterone exposure permits application the spray to other parts of the body e.g. shoulders. Thus, in addition to being safer for the user's partners and children, this product is more convenient to use than existing topical testosterone products.

A very thin layer of solution is formed on the skin when this spray is applied. In only a few minutes, preferably less than 4 minutes, less than 3 minutes, or less than 2 minutes, the solvent/s in the spray evaporate leaving behind a film containing testosterone. During solvent evaporation, the excipients included in the spray prevent recrystallization of testosterone and maintain testosterone in an amorphous state, which is important for its penetration of the skin. Due to this characteristic, it is possible to incorporate a high concentration of testosterone in the formulation. Within about 5 minutes, or preferably about 4 minutes or about 3 minutes, testosterone is absorbed into the skin. The skin then acts as a reservoir from which testosterone is released into the systemic circulation over time. In addition, this film forms a barrier that significantly reduces the potential for transference of testosterone to others, as demonstrated by an in vitro experiment described in Example 5 below.

In some embodiments, the formulation according to the invention is packaged as a bulk solution containing multiple doses in a pump spray system comprising a sealed container fitted with a spray pump, preferably a metering spray pump.

Preferably, the pump system is a pump action spray. Pump action sprays require the application of external pressure for actuation, for example, external manual, mechanical or electrically initiated pressure.

The container holding the solution may be any suitable container for the particular composition, such as a glass, polyethylene, aluminum or steel bottle or canister, or an aluminum pouch within a high density polyethylene bottle. The bottle or canister may be lined with an inert material. The spray pump system may also include a dose indicator or dose counter.

The composition of the invention comprises testosterone, one or more film forming excipients, one or more penetration enhancers, and one or more solvents. The composition may also contain one or more additional optional ingredients, such as one or more solubility enhancers, one or more pH modifiers, one or more viscosity increasing agents and/or one or more fragrances. For example, the composition may contain one or more pH modifiers such as tromethamine. The concentration of the pH modifier may be about 0.05 g/L to about 0.2 g/L. Here, grams per liter (g/L) refers to grams of organic proton acceptor per liter solvent in the composition. In some embodiments, the concentration of the pH modifier is about 0.05 g/L, about 0.1 g/L, or about 0.2 g/L. In some embodiments of the invention the solvent contains Tromethamine.

The film forming excipient is an excipient, preferably a polymer, that is soluble in aliphatic solvents, preferably in ethanol or a mixture of ethanol with other solvents. The film forming excipient is preferably also soluble in aqueous solutions, preferably water, and may be removed from skin using water or water and soap. For film forming excipients having pH dependent solubility, the pH of the aqueous solution must be above or below the specific trigger pH for that excipient to dissolve. For example, some of these film forming excipients dissolve in aqueous solutions only above, pH 6.0, only above pH 7.0, or only below pH 5.0. Therefore, soluble in water as defined herein to mean that the film forming excipient has a solubility in water, at the pH required to dissolve that excipient, that requires 30 parts or less of water (solvent) to dissolve one part of the film forming excipient (solute), or more preferably requires 10 parts of water or less to dissolve one part of the film forming excipient. Thus, the film forming excipient has a solubility in water, at a pH between 1 and 10, that requires 30 parts or less of water (solvent) to dissolve one part of the film forming excipient (solute). For example, the film forming excipient has a solubility requiring 30 parts or less of water (solvent) to dissolve one part of the film forming excipient (solute), when the pH of the water is selected from the group consisting of: below pH 5.0, above pH 4, above pH 5, above pH 5.5, above pH 6, and above pH 7.

Preferably the film forming excipient has a solubility in ethanol that requires 30 parts or less of ethanol (solvent) to dissolve one part of the film forming excipient (solute), or more preferably requires 10 parts or less of ethanol to dissolve one part of the film forming excipient. Solubility is evaluated at room temperature.

Moreover, the film forming excipient, or mixture of film forming excipient with other excipients such as a plasticizer or washability enhancer, prevents recrystallization of testosterone and maintains testosterone in an amorphous state during and after solvent evaporation. This characteristic can be evaluated, for example, by the experiment described in Example 7, or indirectly by the skin penetration experiments described in Examples 3 and 12.

Where the film forming excipient is a mixture of excipients, the mixture should have the desired characteristics.

Examples of film forming excipients that have the desired characteristics include Eudragit® L100 (Methacrylic Acid and Methyl Methacrylate Copolymer 1:1) (which dissolves above pH 6.0), Eudragit® S100 (Methacrylic Acid and Methyl Methacrylate Copolymer 1:2) (which dissolves above pH 7.0), Eudragit® E100 (Poly(butylmethacrylate-co-(2-dimethylaminoethyl)methacrylate-co-methyl methacrylate 1:2:1) (which dissolves below pH 5.0), Hydroxypropyl cellulose (Hypromellose), Ethyl Cellulose, Methyl Vinyl Ether-Maleic Anhydride Copolymers such as Gantrez® ES-435, a Butyl Ester of Methyl Vinyl Ether/Maleic Anhydride Copolymer; and Polyvinyl Acetate-Povidone Polymer (povidone here is a pore former/washability enhancer).

The total concentration of the one or more film forming excipients in the composition is from about 1% w/w to about 20% w/w.

For compositions containing testosterone, when the film forming excipient is an excipient that requires a certain pH to dissolve in water or an aqueous environment, such as Eudragit® S100, a washability enhancer can be included in the composition to make the film more washable, i.e., easier to remove from skin with water or soap and water. In some cases, the washability enhancer also acts as a plasticizer. A preferred washability enhancer is polyethylene glycol, preferably polyethylene glycol 400.

The concentration of washability enhancer in the composition is about 2% to about 20% of the weight of the film forming excipient in the composition. Preferably it is about 8% to about 18% of the weight of the film forming excipient in the composition. Preferably it is about 10%, about 12%, about 13%, about 14%, about 15%, about 16%, about 17%, or about 18% of the weight of the film forming excipient in the composition.

The composition also contains one or more penetration enhancers such as Azone, Glycerol Monooleate, Isopropyl Myristate, Octisalate, Oleic Acid, and/or diethylene glycol monoethyl ether (such as Transcutol® or Transcutol® P). Octisalate and diethylene glycol monoethyl ether are preferred.

The composition also contains one or more solvents such as Acetone, Ethanol and/or Isopropyl Alcohol. Ethanol, and mixtures of ethanol and isopropyl alcohol, are preferred.

The total solvent concentration may be around 50% w/w to about 90% w/w of the composition, but generally will make up the remainder of the weight of the composition and is a sufficient quantity to dissolve the other ingredients.

The composition may also include one or more plasticizers such as Dibutyl Sebacate, Triethyl Citrate, Triacetin, Glycerol, Polyethylene Glycol, and/or Propylene Glycol. The concentration of plasticizer in the composition is preferably about 2% to about 20% of the weight of the film forming excipient in the composition. Preferably it is about 8% to about 18% of the weight of the film forming excipient in the composition. Preferably it is about 10%, about 12%, about 13%, about 14%, about 15%, about 16%, about 17%, or about 18% of the weight of the film forming excipient in the composition. The composition of the present invention may also include other formulation excipients, added, e.g., to achieve a desired consistency or appearance, or to protect the formulation components from degradation and oxidation. Such excipients include, for example, viscosity increasing agents, stabilizing agents, antioxidants, humectants, preservatives, colorant and fragrance agents known in the art of formulation.

Viscosity increasing agents that might be included in the formulation are, e.g., povidone, glycerin, hydroxypropyl cellulose, methylcellulose, and/or carboxymethylcellulose. The concentration of the viscosity increasing agent, if included, is from about 0.5% w/w to about 3% w/w of the composition, preferably from about 1.0% w/w to about 2.5% w/w, and most preferably is about 1.5% w/w.

The composition of the present invention may contain a fragrance or perfume to impart a desired aroma, or to mask odors that may be associated with other components of the composition. If a fragrance is included, the concentration is from about 0.01% w/w to about 5% w/w of the composition, preferably from about 0.1% w/w to about 1% w/w.

Any fragrance suitable for application to the skin can be used herein including a wide variety of fragrances and perfumes that are known to those skilled in the art. The particular perfume used is largely a matter of choice, however, the fragrance should be used at a level effective for providing a noticeable aroma to the composition, or for masking undesired aroma of the composition. Also, the fragrance and whatever carriers accompany it should not impart excessive stinging to the skin, especially broken or irritated skin.

Typical fragrances are described in Arctander, Perfume and Flavour Chemicals (Aroma Chemicals), Vol. I and II (1969, Allured Publishing Corporation, 1969 (ISBN 0931710375, 9780931710377), and Arctander, Perfume and Flavor Materials of Natural Origin (1994, by Allured Pub Corp) (ISBN 0931710367; ISBN13: 9780931710360). Fragrance used in the present invention may also contain solubilizers, diluents, or solvents which are well known in the art.

One embodiment of the invention is a composition comprising more than 10% w/w testosterone; one or more penetration enhancers; one or more solvents; and one or more film forming excipients, wherein the film forming excipient (i) has a solubility in water, at a pH between 1 and 10, that requires 30 parts or less of water to dissolve one part of the film forming excipient; (ii) has a solubility in ethanol that requires 30 parts or less of ethanol to dissolve one part of the film forming excipient; and (iii) can prevent recrystallization of the testosterone and maintain the testosterone in an amorphous state during solvent evaporation when the composition is applied to skin; and wherein the composition is a sprayable liquid solution.

In one embodiment, (i) the concentration in the composition of testosterone is about 12% or higher, (ii) the one or more penetration enhancers is selected from the group consisting of Azone, Glycerol Monooleate, Isopropyl Myristate, Octisalate, Oleic Acid, and diethylene glycol monoethyl ether, (iii) the one or more solvents is selected from the group consisting of Acetone, Ethanol, and Isopropyl Alcohol, (iv) the one or more film forming excipients is selected from the group consisting of Eudragit® L100 (Methacrylic Acid and Methyl Methacrylate Copolymer 1:1), Eudragit® S100 (Methacrylic Acid and Methyl Methacrylate Copolymer 1:2), Eudragit® E100 (Poly(butylmethacrylate-co-(2-dimethylaminoethyl)methacrylate-co-methyl methacrylate 1:2:1), Hydroxypropyl cellulose (Hypromellose).

In another embodiment, (i) the concentration in the composition of testosterone is about 12% or higher, (ii) the one or more penetration enhancers is selected from the group consisting of Azone, Glycerol Monooleate, Isopropyl Myristate, Octisalate, Oleic Acid, and diethylene glycol monoethyl ether, (iii) the one or more solvents is selected from the group consisting of Acetone, Ethanol, and Isopropyl Alcohol, (iv) the one or more film forming excipients is selected from the group consisting of Ethyl Cellulose, Butyl Ester of Methyl Vinyl Ether/Maleic Anhydride Copolymer (Gantrez® ES-435), and Polyvinyl Acetate-Povidone Polymer.

In one embodiment, the composition comprises more than 10% w/w of testosterone. In some embodiments, the concentration of testosterone in the composition is from about 5% w/w to about 30% w/w, or more preferably, is from about 12% w/w to about 25% w/w. In preferred embodiments of the invention, the concentration of testosterone is from about 12% w/w to about 20% w/w, or from about 15% w/w to about 18% w/w. In other preferred embodiments of the invention, the concentration of testosterone is about 12% w/w, about 15% w/w, or about 20% w/w.

In some embodiments of the invention, the concentration of the one or more penetration enhancers in the composition is from about 1% w/w to about 10% w/w, from about 5% w/w to about 15% w/w, from about 7% w/w to about 12% w/w, from about 3% w/w to about 8% w/w, or preferably from about 4% w/w to about 7% w/w.

In some embodiments of the invention, the concentration of the one or more solvents in the composition is from about 60% w/w to about 95% w/w, or about 50% w/w to about 90% w/w. In preferred embodiments of the invention, the solvent is Ethanol USP in a concentration of about 60% w/w to about 75% w/w. In other preferred embodiments, the solvent is a mixture of ethanol and isopropyl alcohol, and the concentration of ethanol is from about 30% w/w to about 80% w/w, or from about 40% w/w to about 65% w/w, and the concentration of isopropyl alcohol is from about 10% w/w to about 40% w/w, or from about 20% w/w to about 30% w/w.

In some embodiments of the invention, the concentration of the one or more film forming excipients in the composition is from about 1% w/w to about 10% w/w, or from about 3% w/w to about 8% w/w, or from about 4% w/w to about 7% w/w.

Another embodiment of the invention is a composition comprising testosterone, octisalate and methacrylic acid and methyl methacrylate copolymer (1:2) (EUDRAGIT® S100), wherein the composition is a liquid.

Another embodiment of the invention is a composition comprising testosterone, octisalate, methacrylic acid and methyl methacrylate copolymer (1:2) (EUDRAGIT® S100), and polyethylene glycol 400, wherein the composition is a liquid.

Yet another embodiment of the invention is a composition comprising testosterone, diethylene glycol monoethyl ether, methacrylic acid and methyl methacrylate copolymer (1:2) (EUDRAGIT® S100), and polyethylene glycol 400, wherein the composition is a liquid.

In some embodiments of the invention, the concentration of octisalate or diethylene glycol monoethyl ether in the composition is from about 1% to about 15%, from about 1% w/w to about 10% w/w, from about 3% w/w to about 8% w/w, from about 5% to about 10%, or from about 4% w/w to about 7% w/w. In preferred embodiments, the concentration of octisalate is about 4% w/w, about 5% w/w, about 6% w/w or about 7% w/w of the composition. In other preferred embodiments, the concentration of diethylene glycol monoethyl ether is from about from about 5% to about 10% w/w.

In some embodiments of the invention, the concentration of methacrylic acid and methyl methacrylate copolymer (1:2) (EUDRAGIT® S100) in the composition is from about 1% w/w to about 10% w/w, from about 3% w/w to about 8% w/w, or from about 4% w/w to about 7% w/w. In preferred embodiments, the concentration of methacrylic acid and methyl methacrylate copolymer (1:2) (EUDRAGIT® S100) is about 4% w/w, about 5% w/w, about 6% w/w or about 7% w/w of the composition.

In some embodiments of the invention, the composition comprises from about 12% w/w to about 20% w/w testosterone USP, from about 40% w/w to about 65% w/w ethanol USP, from about 20% w/w to about 30% w/w isopropyl alcohol USP, from about 4% w/w to about 7% w/w octisalate USP, and from about 4% w/w to about 7% w/w Eudragit® S100 USP/NF (methacrylic acid and methyl methacrylate copolymer (1:2)).

In a preferred embodiment, the concentration of testosterone in the composition is about 12% w/w, the concentration of octisalate in the composition is about 6% w/w, and the concentration of methacrylic acid and methyl methacrylate copolymer (1:2) (EUDRAGIT® S100) in the composition is about 5% w/w.

In other embodiments of the invention, the composition comprises from about 12% w/w to about 25% w/w testosterone USP, from about 60% w/w to about 75% w/w ethanol USP, from about 5% w/w to about 10% w/w diethylene glycol monoethyl ether USP, and from about 4% w/w to about 7% w/w Eudragit® S100 USP/NF (methacrylic acid and methyl methacrylate copolymer (1:2)).

In a preferred embodiment, the concentration of testosterone in the composition is about 17% w/w to about 18% w/w, the concentration of diethylene glycol monoethyl ether in the composition is about 7% w/w to about 10% w/w, and the concentration of methacrylic acid and methyl methacrylate copolymer (1:2) (EUDRAGIT® S100) in the composition is about 4% w/w to about 6% w/w.

In some preferred embodiments, the composition further comprises polyethylene glycol 400 USP-NF in a concentration of about 8% to about 18% of the weight of the film forming excipient in the composition.

The composition is a liquid at room temperature and is sprayable, meaning that the viscosity of the composition allows it to be applied using a spray pump at room temperature. In one embodiment, the composition is contained in a container comprising a spray pump with metering valve. In one embodiment, the viscosity of the composition is less than about 50 cPs, preferably less than about 20 cPs, or less than about 10 cPs. Most preferably the viscosity of the composition is about 4 cPs, about 5 cPs, about 6 cPs, about 7 cPs, about 8 cPs, or about 9 cPs. Viscosity is measured using a viscometer such as a Brookfield Viscometer.

The invention also provides a method of increasing serum testosterone in a human male, by spraying on the skin of a human male this composition. In a preferred embodiment of this method, the amount of testosterone administered in a single application is about 30 mg. This amount of testosterone can be delivered, e.g., in a single actuation of the spray containing 30 mg, or in two actuations each containing 15 mg, or even in more actuations of smaller doses that add up to a total of 30 mg. In addition, after application of the composition, a barrier film is formed within about 5 minutes or less of application, and this film is capable of preventing transfer of testosterone to other persons. This can be evaluated, e.g., by the method described in Example 5. The film formed on the skin is water washable. This can be evaluated, e.g., by the method described in Examples 6 or 10.

In some embodiments of the invention, the composition is administered one to four times per 24 hour period. In other embodiments, the composition is administered one to eight times per 24 hour period. In a preferred embodiment the composition is administered four times per 24 hour period. In some embodiments, a single administration can consist of two spray actuations, such as where each actuation delivers less than 30 mg of testosterone, e.g., where each actuation delivers about 15 mg of testosterone.

If the composition is administered more than once, it can be administered to the same site on the skin as the previous applications. In some embodiments, it is preferred that the additional application/s of the composition is/are applied to a different site on the skin from the previous application/s, or that the film from the previous application/s is washed off the skin before the composition is applied again.

In one embodiment of this method the serum testosterone of the male to which the composition is administered increases by at least 30% over baseline.

In another embodiment, the invention provides a method of administering the composition to provide testosterone replacement therapy in males for conditions associated with a deficiency or absence of endogenous testosterone, such as primary hypogonadism, or hypogonadotropic hypogonadism.

In preferred embodiments, the volume of spray administered is about 500 μL or less, about 400 μL or less, about 300 μL or less, about 250 μL or less, about 200 μL or less, about 150 μL or less, or about 100 μL or less. Most preferably, the volume of spray administered is about 200 uL, about 250 μL or about 100 μL. It is possible to dissolve 30 mg of testosterone (the preferred dose) in a volume less than 250 μL of the composition of the invention, and achieve a testosterone concentration of 20% w/w or higher.

As used herein, unless otherwise specified all formulation ingredient percentages are described as percent weight by weight (% w/w), which refers to the weight of an ingredient as a percentage of the total composition weight.

As used herein, the term "about" means+10% of the value that this term modifies.

As used herein, the term "room temperature" refers to a comfortable ambient temperature, generally taken as 20-25° C.

Several embodiments of the invention are described herein. In addition, the invention is described with reference to the following examples. This invention is not limited to the embodiments or examples described herein. Modifications and variations may suggest themselves and are intended to be within the scope of the appended claims.

EXAMPLES

Example 1: Formulations

Exemplary compositions and a manufacturing process for the testosterone spray are described below:

TABLE 1

COMPOSITIONS 1-3

| Ingredient | Quantity per actuation | | | | | |
|---|---|---|---|---|---|---|
|  | Mg | % w/w | Mg | % w/w | Mg | % w/w |
| Testosterone USP | 30.00 | 12.00 | 30.00 | 12.00 | 30.00 | 12.00 |
| Ethanol USP | 129.65 | 51.86 | 127.25 | 50.90 | 122.37 | 48.95 |
| Isopropyl Alcohol USP | 65.85 | 26.34 | 64.00 | 25.60 | 62.50 | 25.00 |

TABLE 1-continued

COMPOSITIONS 1-3

| Ingredient | Mg | % w/w | Mg | % w/w | Mg | % w/w |
|---|---|---|---|---|---|---|
| Octisalate USP | 12.50 | 5.00 | 15.00 | 6.00 | 15.00 | 6.00 |
| Eudragit ® S100 USP/NF (methacrylic acid and methyl methacrylate copolymer (1:2)) | 10.00 | 4.00 | 12.50 | 5.00 | 17.50 | 7.00 |
| Polyethylene glycol (PEG 400) | 2.00 | 0.8 | 1.25 | 0.5 | 2.63 | 1.05 |
| TOTAL | 250.00 | 100.00 | 250.00 | 100.00 | 250.00 | 100.00 |

TABLE 2

COMPOSITIONS 4-6

| Ingredient | Mg | % w/w | Mg | % w/w | Mg | % w/w |
|---|---|---|---|---|---|---|
| Testosterone USP | 30.00 | 10.00 | 30.00 | 10.00 | 30.00 | 10.00 |
| Ethanol USP | 159.60 | 53.20 | 156.51 | 52.17 | 150.87 | 50.29 |
| Isopropyl Alcohol USP | 81.00 | 27.00 | 78.99 | 26.33 | 76.98 | 25.66 |
| Octisalate USP | 15.00 | 5.00 | 18.00 | 6.00 | 18.00 | 6.00 |
| Eudragit ® S100 USP/NF (methacrylic acid and methyl methacrylate copolymer (1:2)) | 12.00 | 4.00 | 15.00 | 5.00 | 21.00 | 7.00 |
| Polyethylene glycol (PEG 400) | 2.4 | 0.8 | 1.5 | 0.5 | 3.15 | 1.05 |
| TOTAL | 300.00 | 100.00 | 300.00 | 100.00 | 300.00 | 100.00 |

TABLE 3

COMPOSITION 7

| Ingredient | mg | % w/w |
|---|---|---|
| Testosterone USP | 30.00 | 20.00 |
| Ethanol USP | 72.75 | 48.50 |
| Isopropyl Alcohol USP | 30.00 | 20.00 |
| Octisalate USP | 9.00 | 6.00 |
| Eudragit ® S100 USP/NF (methacrylic acid and methyl methacrylate copolymer (1:2)) | 7.50 | 5.00 |
| Polyethylene glycol (PEG 400) | 0.75 | 0.5 |
| TOTAL | 150.00 | 100.00 |

Manufacturing Process:

Ethanol and Isopropyl alcohol are mixed in a suitable vessel. Eudragit® S100 is added to these solvents and the mixture is stirred until a clear solution is formed. Polyethylene glycol is added to this solution, and the mixture is stirred for about 10 minutes. Octisalate is added and the solution is stirred further. Testosterone is added, and the mixture is stirred until a clear solution is achieved. The solution is filled in to a suitable container and a spray pump is affixed to the container.

Example 2: Additional Formulations

Exemplary compositions and a manufacturing process for the testosterone spray are described below:

TABLE 4

COMPOSITIONS 8-10

| Ingredient | Mg | % w/w | Mg | % w/w | Mg | % w/w |
|---|---|---|---|---|---|---|
| Testosterone USP | 30.00 | 12.00 | 30.00 | 12.00 | 30.00 | 12.00 |
| Ethanol USP | 124.75 | 49.90 | 125.75 | 50.30 | 120.00 | 48.00 |
| Isopropyl Alcohol USP | 60.25 | 24.10 | 63.00 | 25.20 | 60.00 | 24.00 |
| Octisalate USP | 12.50 | 5.00 | 15.00 | 6.00 | 17.50 | 7.00 |
| Eudragit ® S100 USP/NF (methacrylic acid and methyl methacrylate copolymer (1:2)) | 17.50 | 7.00 | 12.50 | 5.00 | 17.50 | 7.00 |
| Povidone | 3.75 | 1.50 | 2.50 | 1.00 | 3.75 | 1.50 |
| Fragrance | 1.25 | 0.50 | 1.25 | 0.50 | 1.25 | 0.50 |
| TOTAL | 250.00 | 100.00 | 250.00 | 100.00 | 250.00 | 100.00 |

TABLE 5

COMPOSITIONS 11-13

| Ingredient | Mg | % w/w | Mg | % w/w | Mg | % w/w |
|---|---|---|---|---|---|---|
| Testosterone USP | 30.00 | 10.00 | 30.00 | 10.00 | 30.00 | 10.00 |
| Ethanol USP | 158.40 | 52.80 | 159.90 | 53.30 | 149.40 | 49.80 |
| Isopropyl Alcohol USP | 72.60 | 24.20 | 72.60 | 24.20 | 72.60 | 24.20 |
| Octisalate USP | 12.00 | 4.00 | 18.00 | 6.00 | 21.00 | 7.00 |
| Eudragit ® S100 USP/NF (methacrylic acid and methyl methacrylate copolymer (1:2)) | 21.00 | 7.00 | 15.00 | 5.00 | 21.00 | 7.00 |
| Povidone | 4.5 | 1.50 | 3.00 | 1.00 | 4.5 | 1.50 |
| Fragrance | 1.50 | 0.50 | 1.50 | 0.50 | 1.50 | 0.50 |
| TOTAL | 300.00 | 100.00 | 300.00 | 100.00 | 300.00 | 100.00 |

Manufacturing Process:

Ethanol and Isopropyl alcohol are mixed in a suitable vessel. Eudragit® S100 and Povidone are added to these solvents and the mixture is stirred until a clear solution is formed. Octisalate and Fragrance are added, and the solution is stirred further. Testosterone is added, and the mixture is stirred until a clear solution is achieved. The solution is filled in to a suitable container and a spray pump is affixed to the container.

Example 3: Tape Stripping Study 1

A Tape Stripping Study was performed to compare the penetration profile of a film forming formulation containing Eudragit® S100 and PEG 400 (Formulation A) to that of a non-film forming formulation (Formulation B). Formulations A and B, described in the following table, were evaluated in this tape stripping study:

TABLE 6

| Ingredients | Formulation A | Formulation B |
| --- | --- | --- |
| Ethanol USP | 60.9% w/w | 63.0% w/w |
| Isopropyl Alcohol USP | 27.6% w/w | 28.6% w/w |
| Octisalate USP | 6.0% w/w | 6.0% w/w |
| Methacrylic Acid and Methyl Methacrylate Copolymer (1:2) USP-NF (Eudragit S100 ®) | 5.0% w/w | — |
| Polyethylene glycol (PEG 400) | 0.5% w/w | — |
| Povidone K90 USP | — | 2.4% w/w |
| TOTAL | 100.0% w/w | 100.0% w/w |
| Testosterone USP | 120 mg to QS 1 mL with above solution | 20 mg to QS 1 mL with above solution |

Procedure: Porcine skin was obtained from Stellen Medical and stored in a −20° C. freezer. 100 µl of test formulation was applied to a 25 cm² area of skin surface using a syringe and allowed to dry for 15 minutes. The skin temperature was maintained at 32° C. with a dry block heater. Ten (10) progressive layers of skin surface were removed by tape stripping as follows. Commercial Scotch brand packaging tape was applied to the skin surface and rubbed with lateral finger pressure for 30 seconds. The tape was removed and extracted by shaking for 15 minutes with 20 ml ethanol. The extracted solution was analyzed by HPLC. The amounts of testosterone (% dose) recovered from each layer, as well as the remaining skin, was calculated by comparison to a standard of known testosterone concentration.

The following HPLC instrument and conditions were used to analyze the solutions extracted from the skin samples:

Instrument: Waters Acquity UPLC with PDA detector
Column: Waters Acquity BEH C18 1.7 um 2.1×50 mm
Mobile phase: 60:40 water:acetonitrile
Detection wavelength: 245 nm
Flow: 0.5 ml/min isocratic
Column temperature: 30° C.
Injection volume: 1 µl The results of this study are described in the following table and depicted in FIG. 1:

TABLE 7

Figure 1:
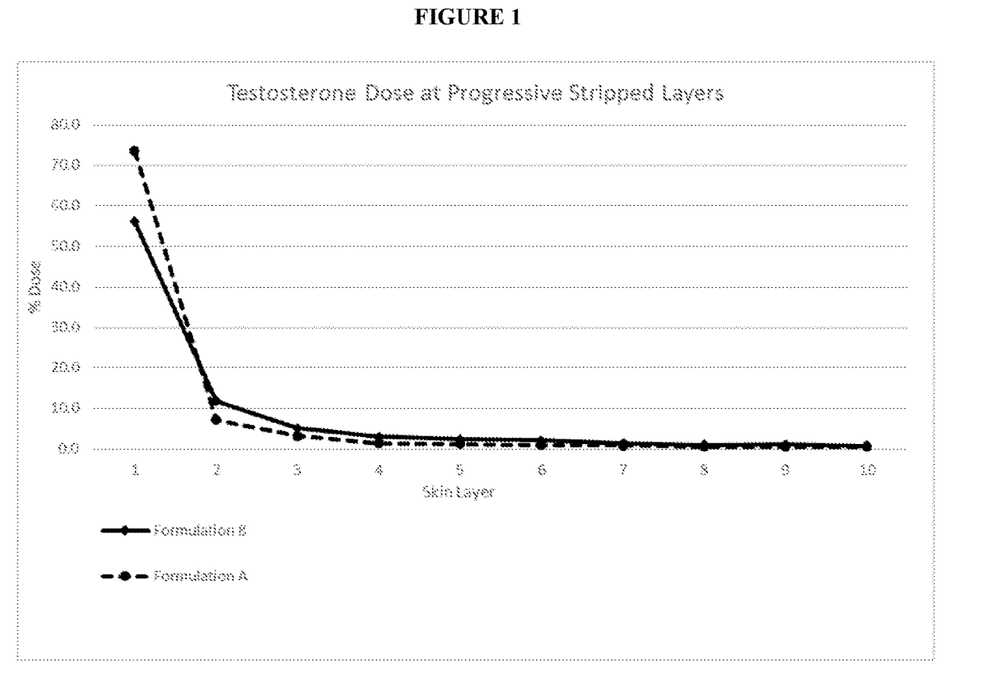
FIG. 1 is a graph depicting the testosterone dose recovered from progressive stripped layers of skin from a tape stripping study performed in porcine skin to compare the penetration profile of a film forming formulation containing Eudragit® S100 to that of a non-film forming formulation.

| | Formulation A | | Formulation B | |
| --- | --- | --- | --- | --- |
| Sample | % Dose average n = 3 | % Dose standard deviation n = 3 | % Dose average n = 6 | % Dose standard deviation n = 6 |
| Layer 1 | 73.5 | 9.3 | 56.0 | 18.6 |
| Layer 2 | 7.2 | 3.6 | 11.8 | 4.7 |
| Layer 3 | 3.2 | 1.0 | 5.1 | 1.8 |
| Layer 4 | 1.3 | 0.5 | 3.0 | 1.2 |
| Layer 5 | 1.2 | 0.2 | 2.4 | 1.2 |
| Layer 6 | 1.0 | 0.7 | 2.1 | 1.0 |
| Layer 7 | 0.9 | 0.4 | 1.3 | 0.7 |
| Layer 8 | 0.5 | 0.3 | 1.0 | 0.8 |
| Layer 9 | 0.5 | 0.4 | 1.0 | 0.7 |
| Layer 10 | 0.5 | 0.5 | 0.7 | 0.3 |
| Remaining skin | 7.4 | 3.7 | 5.9 | 5.2 |
| Sum | 97.2 | 0.7 | 92.9 | 5.7 |
| Sum layers 6-10 & skin | 10.8 | 5.5 | 10.8 | 6.4 |

Conclusion: the penetration depth profiles of Formulations A and B are comparable, which indicates that the film forming spray formulation has similar penetration characteristics as a non-film forming spray formulation, and thus, that the film forming excipient, unexpectedly, is not inhibiting skin penetration of the active ingredient.

Example 4: Tape Stripping Study 2

A Tape Stripping Study was performed to evaluate the reapplication of a dose of a film forming formulation containing Eudragit® S100, wherein the second application is at the same site as the previous application of a dose this film forming formulation.

Formulations A (Testosterone) and A (Placebo), described in the following table, were evaluated in this tape stripping study:

TABLE 8

| Ingredients | Formulation A | Formulation A Placebo |
| --- | --- | --- |
| Ethanol USP | 61.2% w/w | 61.2% w/w |
| Isopropyl Alcohol USP | 27.8% w/w | 27.8% w/w |
| Octisalate USP | 6.0% w/w | 6.0% w/w |
| Methacrylic Acid and Methyl Methacrylate Copolymer (1:2) USP-NF (Eudragit ® S100) | 5.0% w/w | 5.0% w/w |
| TOTAL | 100.0% w/w | 100.0% w/w |
| Testosterone USP | 100 mg to QS 1 mL with above solution | — |

The Tape Stripping Procedure, and HPLC conditions described in Example 3 were used for this evaluation, except that Formulation A (Placebo) was first applied and allowed to dry for 15 minutes. Then Formulation A (Testosterone) was applied over the placebo and allowed to dry before tape stripping was performed.

Figure 2:
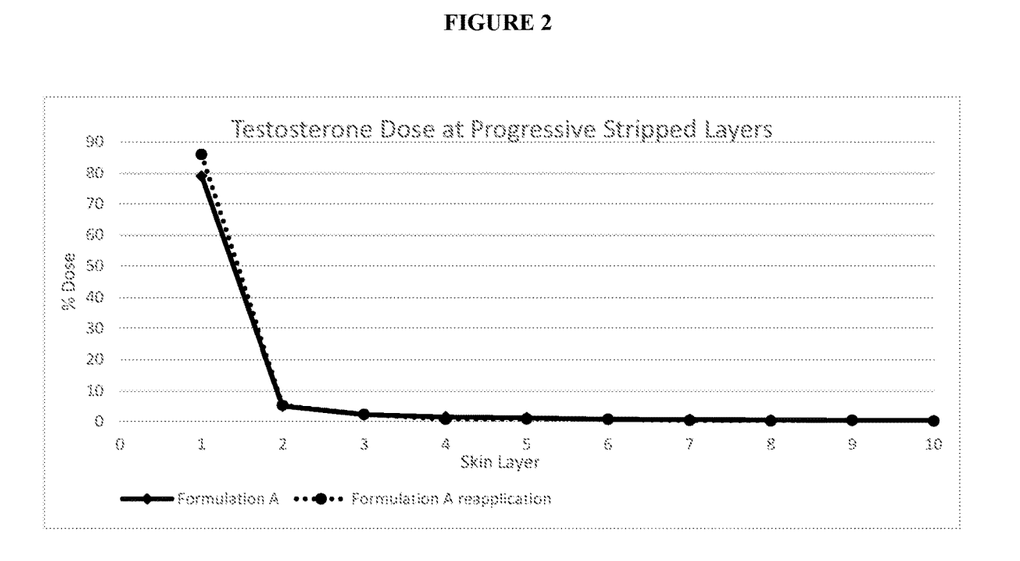
FIG. 2 is a graph depicting the testosterone dose recovered from progressive stripped layers of skin from a tape stripping study performed in porcine skin to evaluate the reapplication of a dose of a film forming formulation containing testosterone and Eudragit® S100 at the same site as a previous application of placebo film forming formulation containing Eudragit® S100.

The results of this study are described in the following table and in FIG. 2:

TABLE 9

| Sample | Formulation A Control | | | Formulation A Reapplication | | |
|---|---|---|---|---|---|---|
| | % Dose replicate 1 | % Dose replicate 2 | % Dose average | % Dose replicate 1 | % Dose replicate 2 | % Dose average |
| Layer 1 | 78.46 | 79.56 | 79.01 | 81.08 | 90.89 | 85.99 |
| Layer 2 | 4.11 | 5.74 | 4.93 | 2.43 | 7.96 | 5.19 |
| Layer 3 | 1.77 | 2.59 | 2.18 | 1.14 | 3.33 | 2.23 |
| Layer 4 | 1.54 | 1.33 | 1.43 | 0.57 | 0.84 | 0.70 |
| Layer 5 | 0.69 | 1.57 | 1.13 | 0.48 | 1.11 | 0.79 |
| Layer 6 | 0.32 | 1.02 | 0.67 | 0.23 | 1.13 | 0.68 |
| Layer 7 | 0.65 | 0.52 | 0.59 | 0.23 | 0.40 | 0.32 |
| Layer 8 | 0.59 | 0.31 | 0.45 | 0.05 | 0.24 | 0.14 |
| Layer 9 | 0.26 | 0.32 | 0.29 | 0.20 | 0.54 | 0.37 |
| Layer 10 | 0.18 | 0.22 | 0.20 | 0.04 | 0.14 | 0.09 |
| Remaining skin | 7.44 | 5.27 | 6.36 | 2.03 | 2.53 | 2.28 |
| Sum | 96.00 | 98.50 | 97.25 | 88.47 | 109.11 | 98.79 |
| Sum layers 6-10 & skin | 9.44 | 7.67 | 8.55 | 2.78 | 4.98 | 3.88 |

Conclusion: Application of Formulation over an existing film delivers less testosterone in deeper skin layers than the control, indicating that not washing off the film residue before reapplication may impact bioavailability of dose if the later application is performed at the same site as the previous application.

Example 5: Skin Contact Transfer Study 1

A skin contact transfer study was performed to compare active ingredient transfer from skin treated with a film forming formulation containing Eudragit® S100 and polyethylene glycol 400 to transfer from skin treated with a non-film forming formulation.

Formulations A (Film Forming) and C (Non-Film Forming), described in the following table, were evaluated in this study:

TABLE 10

| Ingredients | Formulation A | Formulation C |
|---|---|---|
| Ethanol USP | 60.9 | 64.4 |
| Isopropyl Alcohol USP | 27.6 | 29.3 |
| Octisalate USP | 6.0 | 6.3 |
| Methacrylic Acid and Methyl Methacrylate Copolymer (1:2) USP-NF (Eudragit ® S100) | 5.0 | — |
| PEG 400 | 0.5 | — |
| TOTAL | 100.0% w/w | 100.0% w/w |
| Testosterone USP | 120 mg to QS 1 mL with above solution | 120 mg to QS 1 mL with above solution |

Procedure.

Vitro Skin artificial skin was obtained from IMS Inc. Artificial skin was hydrated by incubating it overnight in 15% w/w glycerol chamber followed by 2 hours in 55% RH chamber. 100 ul of formulation A was applied to a 4×5 cm donor piece and allowed to dry for 15 minutes. 100 ul of formulation C was applied to another 4×5 cm donor piece and allowed to dry for 15 minutes. The artificial skin temperature was maintained at 32° C. with a dry block heater. The artificial skin piece as well as a receiver 4×8 cm piece were taped to 0.5-inch acoustic foam pieces of the same size. The donor piece was placed downward facing on top of the receiver piece. A 0.5 kg weight was placed on the donor piece and the weighted piece slowly translated back and forth across the receiver piece 20 times. The residue on the receiver piece was quantitatively transferred by rinsing the receiver piece with ethanol, and the rinse liquid was then diluted to 100 ml with ethanol. These recovered solutions were analyzed by HPLC and the recovered amounts of testosterone were calculated by comparison to a standard of known testosterone concentration.

The Following HPLC Instrument and Conditions were Used to Analyze the Recovered Solutions:
    Instrument: Waters Acquity UPLC with PDA detector
    Column: Waters Acquity BEH C18 1.7 um 2.1×50 mm
    Mobile phase: 60:40 water:acetonitrile
    Detection wavelength: 245 nm
    Flow: 0.5 ml/min isocratic
    Column temperature: 30° C.
    Injection volume: 1 µl The results of this study are described in the following table:

TABLE 11

| Formulation | Replicate results, % transferred |
|---|---|
| Formulation A | 2.0, 1.6 |
| Formulation C | 5.6, 5.5 |

Conclusion: The transfer of testosterone from the film forming formulation containing Eudragit® S100 and polyethylene glycol 400 was substantially less than the transfer of testosterone from the non-film forming formulation. This indicates that the film is effective as a barrier that limits skin to skin transfer of testosterone.

Example 6: Washability Study

A washability study was performed to compare washability from a glass substrate with water and with soap & water of a film forming formulation containing Eudragit® S100 (Formulation W), a film forming formulation containing Eudragit® S100 and a water-soluble component such as polyethylene glycol 400 (Formulation Y), and a formulation containing only testosterone (Formulation X).

Formulations W (Film Forming), Y (Film Forming with water-soluble component), X (Testosterone only), described in the following table, were evaluated in this study:

TABLE 12

| Ingredients | Formulation W | Formulation X | Formulation Y |
|---|---|---|---|
| Ethanol USP | 61.2 | 68.8 | 60.9 |
| Isopropyl Alcohol USP | 27.8 | 31.2 | 27.6 |
| Octisalate USP | 6.0 | — | 6.0 |
| Methacrylic Acid and Methyl Methacrylate Copolymer (1:2) USP-NF (Eudragit ® S100) | 5.0 | — | 5.0 |
| Polyethylene glycol (PEG 400) | — | — | 0.5 |
| TOTAL | 100.0% w/w | 100.0% w/w | 100.0% w/w |
| Testosterone USP | 120 mg to QS 1 mL with above solution | 120 mg to QS 1 mL with above solution | 120 mg to QS 1 mL with above solution |

Procedure: 100 ul of formulation W was applied to a 4×5 cm area on a glass coupon and allowed to dry for 15 minutes. The coupon was dipped in warm water. The coupon was scrubbed with a damp sponge in circular motions for 30 seconds. The dipping and scrubbing steps were repeated. The coupon was dipped in warm water and rinsed with water. The coupon was allowed to dry. The procedure was repeated with formulation X and Y. The entire procedure was then repeated with all formulations using soap & water by applying liquid hand soap to the sponge at the beginning of the washing. Residue remaining on coupons after washing was observed to determine whether film was washed off.

The results of this study are described in the following table:

Conclusion: The film forming formulation containing Eudragit® S100, without polyethylene glycol 400, and the testosterone only formulation both had substantial residue remaining with both water and with soap & water washing procedures indicating that the formulation residue is not washable. The film forming formulation containing Eudragit® S100 and polyethylene glycol 400 had no remaining residue indicating that the film is washable with water and with soap & water. This indicates that the presence of propylene glycol in the film forming formulation increases washability of film with water and with soap & water.

Example 7: Crystallization Study

This study was performed to evaluate whether testosterone crystallized from the film forming formulation following evaporation of the formulation solvent on a glass substrate, and to determine whether the film forming excipient or washability enhancer impact the crystallization of testosterone. The following formulations were evaluated.

TABLE 14

| Ingredients | Formulation W | Formulation X2 | Formulation Y |
|---|---|---|---|
| Ethanol USP | 61.2% w/w | 64.7% w/w | 60.9% w/w |
| Isopropyl Alcohol USP | 27.8% w/w | 29.3% w/w | 27.6% w/w |
| Octisalate USP | 6.0% w/w | 6.0% w/w | 6.0% w/w |
| Methacrylic Acid and Methyl Methacrylate Copolymer (1:2) USP-NF (Eudragit S100 ®) | 5.0% w/w | — | 5.0% w/w |
| Polyethylene glycol 400 USP-NF | — | — | 0.5% w/w |
| TOTAL | 100.0% w/w | 100.0% w/w | 100.0% w/w |
| Testosterone USP | 120 mg to QS 1 mL with above solution | 120 mg to QS 1 mL with above solution | 120 mg to QS 1 mL with above solution |

TABLE 13

| Formulation | Washability with Water | Washability with Soap and Water |
|---|---|---|
| Formulation W | Substantial residue remaining | Substantial residue remaining |
| Formulation X | Substantial residue remaining | Substantial residue remaining |
| Formulation Y | No residue remaining | No residue remaining |

Procedure.

A Hamilton syringe was used to spray 10 µL of each formulation onto a 0.8 cm² silicon wafer plate. Each plate was then stored for 20 minutes RT (22° C./~50% RH (ambient RH) before samples were taken.

Samples were collected at the edge and center of the plate using a spatula. The samples were evaluated by Two Dimensional powder X-ray diffractometry (2DPXRD). The instrument used was a D8 Discover, Bruker 2D X-ray diffractometer. Cobalt was used as the source and the collimator setting was 800 microns beam diameter. The testosterone crystal structures were retrieved from CSD and the obtained XRD patterns were compared with reported CSD crystal structures.

Figure 3:
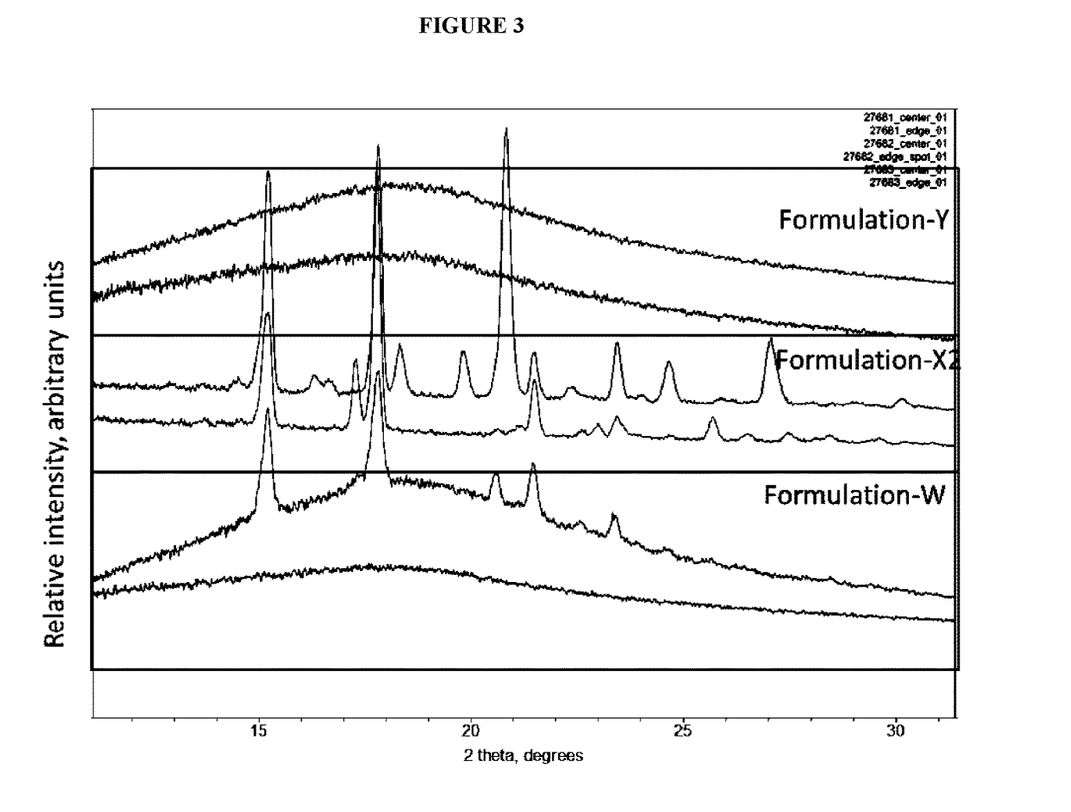
FIG. 3 depicts an overlay of the 2DPXRD Patterns for samples taken from silicon wafer plates treated with formulations W, X2 or Y.

The results for each sample are shown in FIG. 3.

Conclusions: For Formulation W, evaluation by 2DPXRD indicates that the precipitate at the center of the sample was amorphous by 20 minutes, but that the precipitate at the edge showed characteristic peaks of anhydrous form. For Formulation X2, the precipitate at the center of the sample showed characteristic peaks of anhydrous form, but the precipitate at the edge appeared to be a mixture of anhydrous and hydrate forms. For Formulation Y, the precipitate at the center and edge of the sample were amorphous by 20 minutes.

Example 8: Additional Formulations

The following film forming compositions contain ethanol as solvent, and Transcutol® P as penetration enhancer.

TABLE 15

Composition 14

| Ingredients | Quantity (mg) | % w/w | % w/v |
| --- | --- | --- | --- |
| Ethanol USP | 116.40<br>144.60 µL<br>(qs to 200 µL) | 67.75 | 72.30 |
| Methacrylic acid and methyl methacrylate copolymer (1:2) (Eudragit ® S100) USP-NF | 8.00 | 4.66 | 4.00 |
| Diethylene glycol monoethyl ether (Transcutol ® P) USP-NF | 16.00 | 9.31 | 8.00 |
| Polyethylene glycol 400 USP-NF | 1.40 | 0.82 | 0.70 |
| Testosterone USP | 30.00 | 17.46 | 15.00 |
| TOTAL | 171.80 | 100.00 | 100.00 |

TABLE 16

Composition 15

| Ingredients | Quantity (mg) | % w/w | % w/v |
| --- | --- | --- | --- |
| Ethanol USP | 116.48<br>144.70 µL<br>(qs to 200 µL) | 67.81 | 72.35 |
| Methacrylic acid and methyl methacrylate copolymer (1:2) (Eudragit ® S100) USP-NF | 8.80 | 5.12 | 4.40 |
| Diethylene glycol monoethyl ether (Transcutol ® P) USP-NF | 15.00 | 8.73 | 7.50 |
| Polyethylene glycol 400 USP-NF | 1.50 | 0.87 | 0.75 |
| Testosterone USP | 30.00 | 17.47 | 15.00 |
| TOTAL | 171.78 | 100.00 | 100.00 |

TABLE 17

Composition 16

| Ingredients | Quantity (mg) | % w/w | % w/v |
| --- | --- | --- | --- |
| Ethanol USP | 116.89<br>145.20 µL<br>(qs to 200 µL) | 68.08 | 72.60 |
| Methacrylic acid and methyl methacrylate copolymer (1:2) (Eudragit ® S100) USP-NF | 7.50 | 4.37 | 3.75 |
| Diethylene glycol monoethyl ether (Transcutol ® P) USP-NF | 16.50 | 9.61 | 8.25 |
| Polyethylene glycol 400 USP-NF | 0.80 | 0.47 | 0.40 |
| Testosterone USP | 30.00 | 17.47 | 15.00 |
| TOTAL | 171.69 | 100.00 | 100.00 |

Manufacturing Process:

Ethanol is added to a suitable vessel. Eudragit® S100 is added and the ingredients stirred until a clear solution is formed. Next Transcutol® P and Polyethylene glycol 400 are added and the mixture is stirred for about 15 minutes. Finally, Testosterone is added, and the mixture is stirred until a clear solution is formed. The solution is filled into a suitable container and a spray pump is affixed to the container.

Example 9: Breathability Study

Procedure: A film forming formulation containing ethanol, testosterone, diethylene glycol monoethyl ether, methacrylic acid and methyl methacrylate copolymer (1:2) (EUDRAGIT® S100), and polyethylene glycol 400, was applied to the surface of porous surgical tape (Transpore™, 3M, St. Paul, MN) membrane at 12.5 µl per cm$^2$ and allowed to dry. A water vapor impermeable container with an opening at the top was partially filled with water. The spray was applied to the porous tape, which was placed over the opening of the container. The container was stored in a humidity chamber at 37° C. in the presence of calcium chloride desiccant, which maintained a low humidity within the chamber. Water loss from the container over time was determined gravimetrically by periodically measuring the container weight over a period of at least 48 hours, and a water vapor transmission rate per area was determined. Two reference control evaluations were also performed—a non-occluded control with only the porous tape and an occluded control in which the porous tape was covered with non-porous packaging tape.

Figure 4:
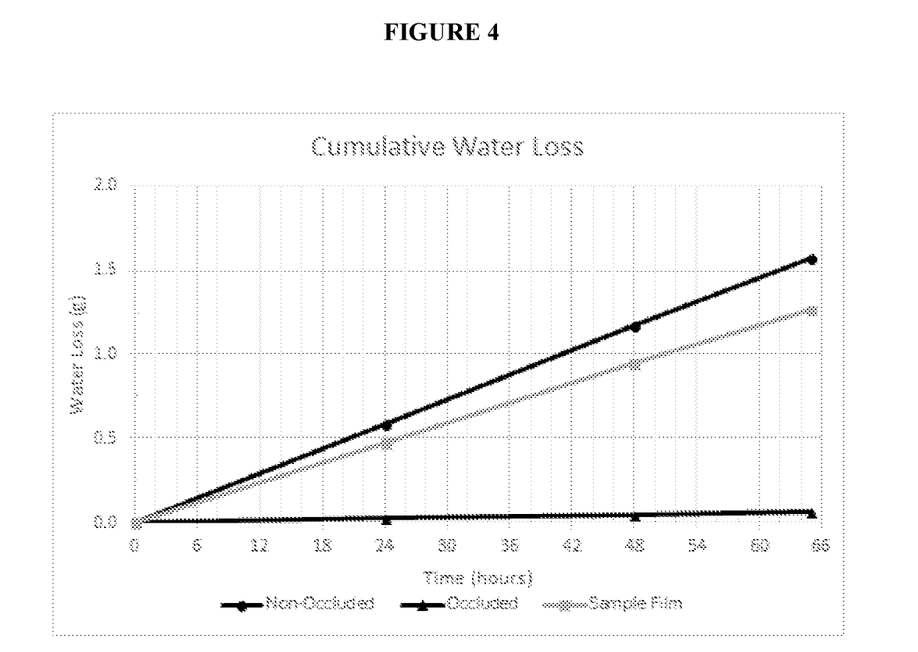
FIG. 4 is a graph depicting the cumulative water loss from water filled bottles covered with a porous membrane treated with a film forming formulation, an occluded porous membrane, or a non-occluded porous membrane.

The sample with the film forming formulation had a mean water vapor transmission rate of 1743 g/m2/24 hours, and this rate as a fraction relative to the non-occluded control was 0.80. The relative transmission result is derived from the equation (sample mean rate-occluded control mean rate)/(non-occluded control mean rate-occluded control mean rate). The results are depicted in FIG. 4.

This high water vapor transmission rate relative to the non-occluded control indicates that this film forming formulation is not obstructing water vapor transmission.

Example 10: In Vitro Film Washability Study

An in vitro study was also conducted to determine if residual drug left on the skin once the film has been washed off.

Procedure: A film forming formulation containing ethanol, testosterone, diethylene glycol monoethyl ether, methacrylic acid and methyl methacrylate copolymer (1:2) (EUDRAGIT® S100), and polyethylene glycol 400, was applied to excised porcine abdominal skin and allowed to dry for 15 minutes. The skin was washed by wiping with a wet soft sponge for 1 minute with periodic dipping in warm water and then wiped with an alcohol wipe. In another experiment, the skin surface with the film was wiped only with an alcohol wipe to remove the film without washing. Any residual testosterone in the wipes was quantitated. Results: 5% of the applied dose was recovered from the skin surface after washing with water compared to 84% for an unwashed control sample where the film is wiped off with an alcohol wipe.

The ability to wash off the film off of the skin is important so that the patient has the option to apply the subsequent dose at the previous site of application. In vitro testing, demonstrated that the film can be washed off in less than a minute with water or soap and water.

Example 11: In Vitro Permeation Study

Formulation differences can impact drug bioavailability. An in vitro study was conducted to compare the permeation of the film forming formulation against a reference product of Axiron using Franz diffusion cells.

Procedure: Franz cells with a donor area of 4.9 cm² and 20 ml receptor chamber volume were used. The cells were assembled with excised abdominal porcine skin and the receptor chamber was filled with 50:50 ethanol:water media. The samples tested were (1) a film forming formulation containing ethanol, testosterone, diethylene glycol monoethyl ether, methacrylic acid and methyl methacrylate copolymer (1:2) (EUDRAGIT® S100), and polyethylene glycol 400, and (2) Axiron®. The film forming formulation contained 15% w/v testosterone, and Axiron® contained 2% w/v testosterone. For each sample, 60 µl of the formulation was added to the donor chamber of the cell. The samples were maintained at 32° C. in an oven and the receptor chamber solution was magnetically stirred to maintain homogeneity. Samples were collected 1, 2, 4, 6, and 24 hours post application.

Figure 5:
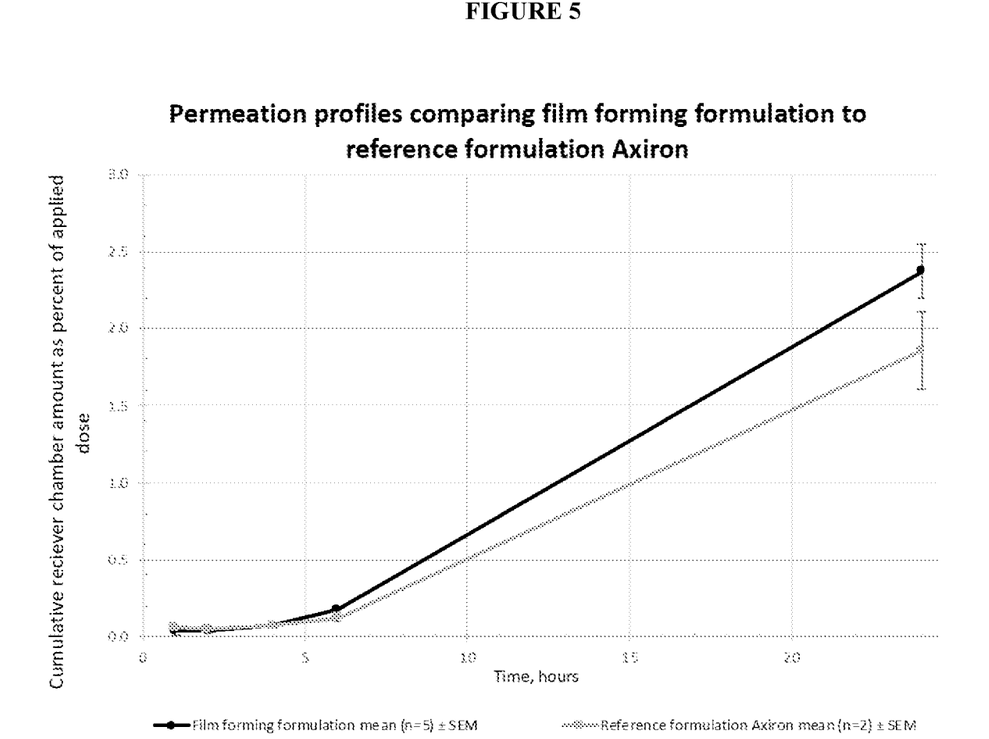
FIG. 5 shows the permeation profiles for testosterone recovered from porcine skin samples treated with a film forming formulation containing Eudragit® S100 with a non-film forming formulation, AXIRON®.

Results: Permeation profiles indicate that testosterone from the film forming formulation permeates at a rate that is not lower than reference formulation Axiron. Permeation results are presented in FIG. 5.

Example 12: Tape Stripping Study

Figure 6:
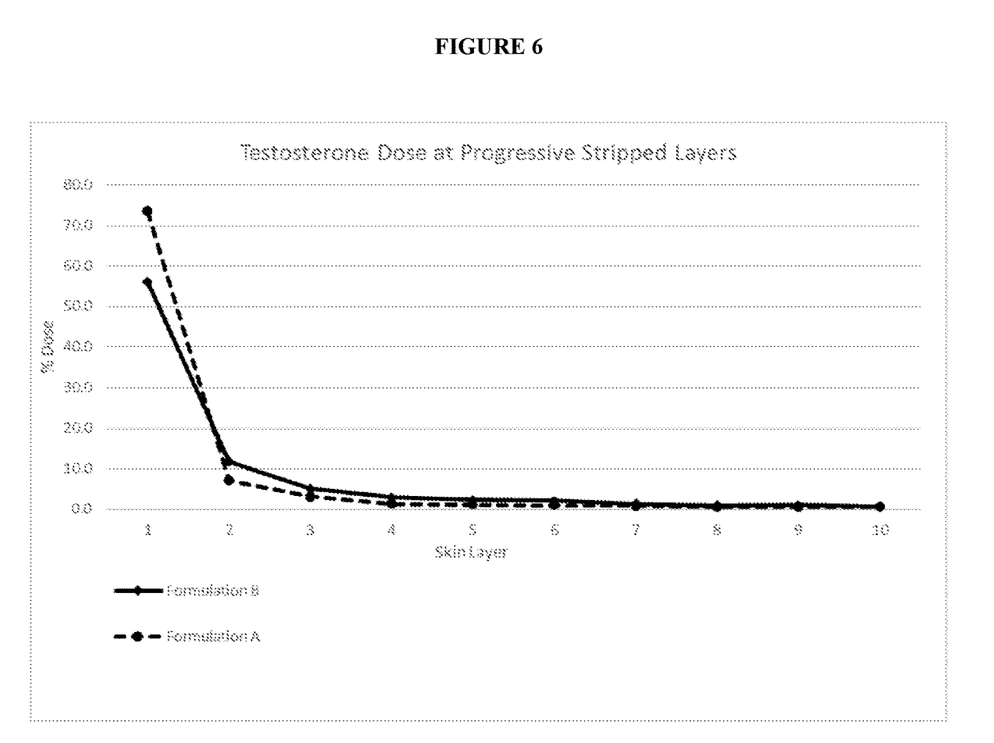
FIG. 6 is a graph depicting the testosterone dose recovered from progressive stripped layers of skin from a tape stripping study performed in porcine skin to compare the penetration profile of a film forming formulation containing Eudragit® S100 with a non-film forming formulation, AXIRON®.

A tape stripping study was performed to compare the penetration profiles of the drug through various levels of the skin. In this study, a film forming formulation containing ethanol, testosterone, diethylene glycol monoethyl ether, methacrylic acid and methyl methacrylate copolymer (1:2) (EUDRAGIT® S100), and polyethylene glycol 400 (Formulation A) to that of the Axiron® formulation (Formulation B). The results are depicted in FIG. 6.

Procedure: Porcine skin was obtained from Stellen Medical and stored in a −20° C. freezer. 100 µl of test formulation was applied to a 25 cm² area of skin surface using a syringe and allowed to dry for 15 minutes. The skin temperature was maintained at 32° C. with a dry block heater. Ten (10) progressive layers of skin surface were removed by tape stripping as follows: Commercial Scotch brand packaging tape was applied to the skin surface and rubbed with lateral finger pressure for 30 seconds. The tape was removed and extracted by shaking for 15 minutes with 20 ml ethanol. The extracted solution was analyzed by HPLC. The amount of testosterone (% dose) recovered from each layer, as well as in the remaining skin, was calculated by comparison to a standard of known testosterone concentration. Conclusion: The drug penetration profiles indicate that the film forming spray (Formulation A) has similar drug penetration characteristics to that of a non-film forming solution of Axiron® (Formulation B).

What is claimed is:

1. A composition comprising
   a. 10% to 25% w/w testosterone;
   b. one or more penetration enhancers;
   c. one or more solvents;
   d. about 4% to about 8% of a film forming excipient, where the film forming excipient is poly(butylmethacrylate-co-(2-dimethylaminoethyl)methacrylate-co-methyl methacrylate 1:2:1; and
   e. one or more washability enhancers, wherein the washability enhancer is about 8% to about 20% the weight of the film forming excipient,
   wherein the film forming excipient (i) has a solubility in water, at a pH between 1 and 10, that requires 30 parts or less of water to dissolve one part of the film forming excipient, (ii) has a solubility in ethanol that requires 30 parts or less of ethanol to dissolve one part of the film forming excipient, and (iii) can prevent crystallization of the testosterone and maintain the testosterone in an amorphous state during solvent evaporation when the composition is applied to skin, and wherein the composition is a sprayable liquid solution.

2. The composition of claim 1, wherein the washability enhancers comprise a polyethylene glycol.

3. The composition of claim 1, wherein the composition is capable of preventing transfer of testosterone from the composition to other persons.

4. The composition of claim 1, wherein the composition is contained in a container comprising a spray pump with metering valve.

5. A composition comprising (a) at least about 12% w/w testosterone, (b) one or more penetration enhancers selected from the group consisting of azone, glycerol monooleate, isopropyl myristate, octisalate, oleic acid, and diethylene glycol monoethyl ether, (c) one or more solvents selected from the group consisting of acetone, ethanol, and isopropyl alcohol, (d) about 4% to about 8% of a film forming excipient, where the film forming excipient is poly(butylmethacrylate-co-(2-dimethylaminoethyl)methacrylate-co-methyl methacrylate 1:2:1, and (e) one or more washability enhancers, wherein the washability enhancer is about 8% to about 20% the weight of the film forming excipient.

6. The composition of claim 5, wherein the washability enhancer comprises a polyethylene glycol.

7. The composition of claim 5, wherein the penetration enhancer comprises diethylene glycol monoethyl ether or octisalate.

8. The composition of claim 6, wherein the polyethylene glycol is polyethylene glycol 400.

9. The composition of claim 5, wherein the composition is capable of preventing transfer of testosterone from the composition to other persons.

10. The composition of claim 5, wherein the composition is contained in a container comprising a spray pump with metering valve.

11. A composition comprising (a) at least 10% w/w testosterone, (b) about 4% to about 8% poly(butylmethacrylate-co-(2-dimethylaminoethyl)methacrylate-co-methyl methacrylate 1:2:1, (c) a washability enhancer, and (d) a penetration enhancer, wherein the composition is a sprayable liquid.

12. The composition of claim 11, wherein the concentration of poly(butylmethacrylate-co-(2-dimethylaminoethyl)methacrylate-co-methyl methacrylate 1:2:1 in the composition is about 4% w/w to about 7% w/w, and the concentration of penetration enhancer is about 5% w/w to about 10% w/w.

13. The composition of claim 11, wherein the concentration of testosterone in the composition is about 12% w/w to about 25% w/w.

14. The composition of claim 11, wherein the composition further comprises one or more solvents selected from the group consisting of acetone, ethanol, and isopropyl alcohol.

15. The composition of claim 11, wherein the composition further comprises about 60% w/w to about 75% w/w/ethanol USP.

16. The composition of claim 11, wherein the washability enhancer comprises polyethylene glycol.

\* \* \* \* \*